(12) United States Patent
Saunders et al.

(10) Patent No.: US 10,835,270 B2
(45) Date of Patent: Nov. 17, 2020

(54) SURGICAL SNARE

(71) Applicant: CREO MEDICAL LIMITED, Chepstow (GB)

(72) Inventors: Brian Saunders, Rickmansworth (GB); Sandra May Bernadette Holmes, Stevenage (GB); Craig Gulliford, Chepstow (GB); Steven Morris, Chepstow (GB); Christopher Paul Hancock, Bath (GB)

(73) Assignee: CREO MEDICAL LIMITED, Chepstow (GB)

( * ) Notice: Subject to any disclaimer, the term of this patent is extended or adjusted under 35 U.S.C. 154(b) by 629 days.

(21) Appl. No.: 15/518,725

(22) PCT Filed: Oct. 16, 2015

(86) PCT No.: PCT/EP2015/074004
§ 371 (c)(1),
(2) Date: Apr. 12, 2017

(87) PCT Pub. No.: WO2016/059210
PCT Pub. Date: Apr. 21, 2016

(65) Prior Publication Data
US 2017/0231647 A1 Aug. 17, 2017

(30) Foreign Application Priority Data
Oct. 16, 2014 (GB) .................................. 1418368.5

(51) Int. Cl.
*A61B 17/22* (2006.01)
*A61B 17/221* (2006.01)
(Continued)

(52) U.S. Cl.
CPC ...... *A61B 17/221* (2013.01); *A61B 17/32056* (2013.01); *A61B 2017/00353* (2013.01);
(Continued)

(58) Field of Classification Search
CPC ............ A61B 17/221; A61B 17/32056; A61B 2017/00353; A61B 2017/22079;
(Continued)

(56) References Cited

U.S. PATENT DOCUMENTS 4,538,611 A  9/1985 Kelman
4,718,419 A  1/1988 Okada
(Continued)

FOREIGN PATENT DOCUMENTS

AU  2001233500 B2  2/2005
CN  2745521 Y  12/2005
(Continued)

OTHER PUBLICATIONS

Communication dated Dec. 5, 2018, from the State Intellectual Property Office of People's Republic of China in counterpart Application No. 201580056221.3.
(Continued)

*Primary Examiner* — Erich G Herbermann
(74) *Attorney, Agent, or Firm* — Arent Fox LLP

(57) ABSTRACT

Embodiments of the invention provide a surgical snare structure in which the material used for the snare and the deployment mechanism of the snare are configured to improve the cutting efficacy of the snare. In particular, the surgical snare structure of the invention may omit the kink or nib present in the loop of known surgical snares and/or may provide a reaction surface against which the cutting action of the snare is effective. The surgical snare of the invention may be a cold, i.e. mechanical-only effect, snare, or may be used in conjunction with radiofrequency (RF) and/or microwave energy to enhance a cutting or coagulation effect.

14 Claims, 4 Drawing Sheets

(51) Int. Cl.
*A61B 17/3205* (2006.01)
*A61B 17/00* (2006.01)

(52) U.S. Cl.
CPC .............. *A61B 2017/2212* (2013.01); *A61B 2017/22079* (2013.01)

(58) Field of Classification Search
CPC ........ A61B 2017/2212; A61B 10/0045; A61B 10/0038; A61B 10/02; A61B 10/06; A61B 2010/0208; A61B 2010/0216; A61B 2010/0225
See application file for complete search history.

(56) References Cited

U.S. PATENT DOCUMENTS

| | | | |
|---|---|---|---|
| 2003/0135222 A1 | 7/2003 | Baska | |
| 2004/0220604 A1 | 11/2004 | Fogarty et al. | |
| 2006/0173408 A1 | 8/2006 | Simmon et al. | |
| 2006/0253128 A1* | 11/2006 | Sekine | A61B 17/00234 606/139 |
| 2009/0036899 A1 | 2/2009 | Carlton et al. | |
| 2009/0088778 A1* | 4/2009 | Miyamoto | A61B 17/0401 606/144 |
| 2009/0182324 A1 | 7/2009 | Kurtulus | |
| 2011/0106107 A1* | 5/2011 | Binmoeller | A61B 17/0487 606/139 |
| 2012/0022558 A1* | 1/2012 | Friedman | A61B 17/12013 606/139 |

FOREIGN PATENT DOCUMENTS

| | | |
|---|---|---|
| CN | 101111198 A | 1/2008 |
| DE | 3626371 A1 | 2/1987 |
| JP | 48-2474 | 1/1973 |
| JP | 10-14922 A | 1/1998 |
| JP | 2000-14631 A | 1/2000 |
| JP | 2005-270464 A | 10/2005 |
| JP | 2006-334398 A | 12/2006 |
| WO | WO 93/21845 A1 | 11/1993 |
| WO | WO 01/60265 A1 | 8/2001 |
| WO | WO 2006/081545 A1 | 8/2006 |
| WO | WO 2013/103934 A1 | 7/2013 |

OTHER PUBLICATIONS

Communication from the State Intellectual Property Office of People's Republic of China in counterpart Application No. 201580056221.3, dated Jul. 17, 2019.
Communication from the Japanese Patent Office in counterpart application No. 2017-520455, dated Jun. 18, 2019.
International Search Report and Written Opinion of related foreign application PCT/EP2015/074004 dated Jan. 13, 2016.
Written Opinion for corresponding Singapore Application No. 11201703052U dated Feb. 19, 2018.
British Search Report of related British Patent Application No. 1418368.5 dated Mar. 24, 2015.
Combined British Search and Examination Report of related British Patent Application No. 1518324.7 dated Mar. 22, 2016.

* cited by examiner

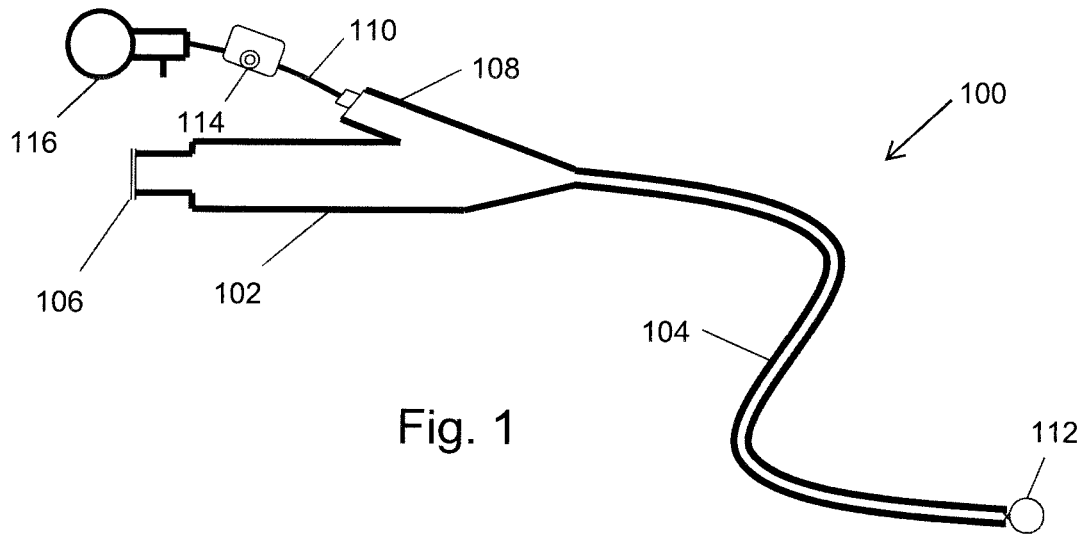
Fig. 1
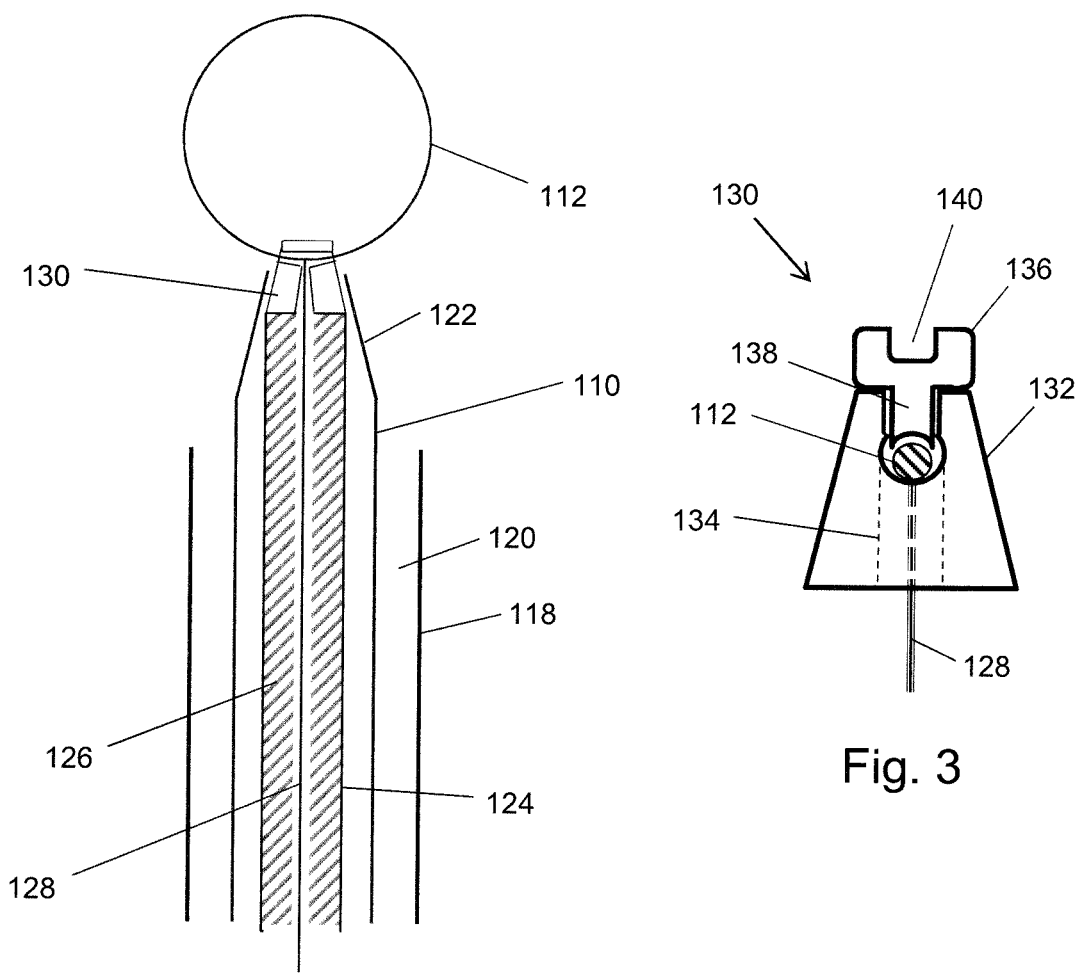
Fig. 2
Fig. 3

SURGICAL SNARE

CROSS-REFERENCE TO RELATED APPLICATIONS

This application is a National Stage Entry of International Patent Application No. PCT/EP2015/074004, filed Oct. 16, 2015, which claims priority to British Patent Application No. 1418368.5, filed Oct. 16, 2014. The disclosures of the priority applications are incorporated in their entirety herein by reference.

FIELD OF THE INVENTION

The invention relates to a surgical snare, i.e. a surgical instrument having a retractable loop of material for gripping or cutting through a stem of biological tissue, e.g. in a polypectomy procedure. In particular, the invention relates to a surgical snare capable of introduction via a catheter through an instrument channel of a scoping device (e.g. endoscope or colonoscope).

BACKGROUND TO THE INVENTION

It is well known to use surgical snares in polypectomy procedures. Conventional snares comprise a loop of wire that is slidable within a hollow sheath. The loop of wire is resilient so that when it is extended beyond the sheath, it tends to open to create a round space for hooking over a polyp. To grip or remove the polyp, the loop of wire is then retracted back into the hollow sheath, whereby the area of the round space decreases and the wire contacts and ultimately cuts through the stem of the polyp.

Typically, the distal end of the loop of wire has a kink or nib formed therein, which helps to prevent the shape of the wire distorting as it is retracted.

To assist with cutting, it is known to deliver radiofrequency (RF) energy through the snare as a means of performing diathermy on biological tissue held by the snare. Snares which operate with such energy are often referred to as "hot" snares. Snares which operate purely mechanically are often referred to as "cold" snares.

SUMMARY OF THE INVENTION

At its most general, the present invention proposes a surgical snare structure in which the material used for the snare and the deployment mechanism of the snare are configured to improve the cutting efficacy of the snare. In particular, the surgical snare structure of the invention may omit the kink or nib present in the loop of known surgical snares and/or may provide a reaction surface against which the cutting action of the snare is effective. The surgical snare of the invention may be a cold, i.e. mechanical-only effect, snare, or may be used in conjunction with radiofrequency (RF) and/or microwave energy to enhance a cutting or coagulation effect.

According to one aspect of the invention there is provided a surgical snare, preferably a cold (RF-free) surgical snare, comprising: a flexible actuator shaft comprising an outer sleeve and an inner push rod mounted within (e.g. coaxially with) and slidable relative to the outer sleeve; an end cap mounted at a distal end of the outer sleeve; a loop of wire, preferably a nibless loop of wire, connected to a distal end of the inner push rod, wherein the end cap includes a passageway for receiving the nibless loop of wire, whereby the inner push rod is operable to retract the nibless loop of wire into the end cap, and wherein the end cap includes a reaction surface at its distal end against which the nibless loop of wire bears when fully retracted into the end cap. Herein, the term "nibless" may mean "formed without a kink or other discontinuity, i.e. having the same sense of curvature along its entire length. In other words, the loop of wire has no changes in the direction of curvature around the loop.

The combination of a nibless loop of wire and a reaction surface against which cutting can be performed may enable the snare to perform a cleaner cut. This may be particular useful in the removal of small amounts of biological tissue, such as the small sessile polyps that are encountered in colonoscopy procedures. A clean cut may enable better en-bloc removal of biological tissue, i.e. a more complete excision, which reduces or eliminates the presence of rugged tissue following cutting. Rugged tissue has been associated with a high risk of polyp regrowth, so it is desirable to make the cut as clean as possible.

Moreover, the use of heating effects (diathermy) in the colon may also be undesirable because of the risk of delayed bleeding. The present invention proposes a solution that does not require heating, and therefore eliminates this risk. However, in other embodiments, additional heating effects may be useful. The snare of the invention may thus also incorporate means for delivering RF and/or microwave energy.

The reaction surface may be a flat or concave distal face of the end cap. The shape may be selected to form a circular aperture with the loop of wire as it is retracted. The radius of the concave surface may be the same as the loop of wire when fully extended. This arrangement ensures that the lesion created by the snare is circular and reduces or minimises the forces on the tissue during the cut. It is desirable for there to be no gap between the reaction surface and loop of wire when the loop of wire is fully retracted. It is therefore preferable for the loop of wire to be fully retractable into the end cap.

The reaction surface may include a groove for receiving the nibless loop of wire when fully retracted into the end cap.

The reaction surface may be on a distally facing surface of the end cap. Alternatively, it may be formed on one side of the end cap, whereby the passageway in the end cap is arranged to direct the loop of wire sideways out of the end cap when it is extended using the push rod. Opening the snare loop to one side of the end cap may assist in gripping tissue within the loop of wire.

In some circumstances, it may be desirable to deliver electromagnetic energy to the nibless loop of wire to enhance a cutting function or to aid coagulation. In one example, radiofrequency (RF) and/or microwave energy may be delivered to the end cap along a coaxial cable that runs through or alongside the flexible actuator shaft. The nibless loop of wire may comprise one or more conductive portions electrically connected with an inner conductor of the coaxial cable, and the reaction surface may include one or more conductive portions electrically connected to an outer conductor of the coaxial cable. The conductive portions on the nibless loop of wire and reaction surface may thus form a bipolar structure for transmitting RF energy and/or microwave energy into the biological tissue gathered by the nibless loop of wire.

The flexible actuator shaft may represent a catheter within which the inner push slides to actuate the snare. The end cap may thus be attached at the distal end of the catheter. However, in another example, the surgical snare may comprise an additional catheter, wherein the flexible actuator shaft is slidably mounted in the catheter to deploy the end cap at a distal end thereof. The catheter may be sized to fit within the instrument channel of a scoping device, e.g. colonoscope. In use, the catheter may thus be inserted in the instrument channel while the flexible actuator shaft is either absent from the interior thereof or in a retracted configuration in which the end cap is spaced proximally from a distal end of the catheter. After the colonoscope is positioned at the treatment site, the flexible actuator shaft may slide axially in the catheter to position the end cap at the distal end thereof. The inner push rod can then be used to operate the snare, e.g. by deploying the loop of wire.

The catheter may have a tip section that narrows, e.g. conically, towards a distal end of the catheter. This configuration may assist in the precise positioning of the loop of wire. The end cap may be shaped to abut the inner surface of the tip section, e.g. in a manner that enable repeatable accurate positioning of the loop of wire and reaction surface. The snare may be lockable in this configuration.

There may be a fluid flow path around the end cap, e.g. between an outer surface of the catheter and an inner surface of an instrument channel through which the catheter is introduced, or between an inner surface of the catheter and the flexible actuator/end cap, to permit a suction force to be applied beyond the distal end of the catheter. It may be useful to apply a suction force during treatment to assist capture of a polyp within the loop of wire and/or to remove fluid from the treatment site.

In one embodiment, the nibless loop of wire comprises a fixed circumference loop formed from a length of wire whose two ends are attached together. The fixed circumference loop may be mounted in the end cap after the two ends are attached together, e.g. by forming the end cap as two parts which are secured together after the loop of wire is mounted therein. This configuration ensures that operation of the inner push rod causes both sides of the loop of wire to be retracted into the end cap simultaneously. The biological tissue captured in the loop may thus be drawn towards the reaction surface in an uniform manner. The fixed circumference loops may have predetermined diameters, e.g. 3 mm, 6 mm, 8 mm, 10 mm, 12 mm or the like.

The nibless loop of wire may be connected to the inner push rod at a junction between the two ends of the length of wire. The length of wire may be a shape memory alloy (e.g. nitinol) which tends to adopt a round shape, e.g. a circle having a diameter of 10 mm or less, preferably 8 mm of less. In one example, the shape memory properties of the length of wire may be used to train the loop of wire to adopt a useful shape for operation of the snare at a given temperature. The temperature of the loop of wire may be controlled by delivering a current (e.g. small DC or RF AC) to the loop of wire. In one example, the trained useful shape may be a loop of wire of increased rigidity, which may assist in locating the loop over a polyp.

The end cap may be arranged to deflect the nibless loop of wire as it extends distally therefrom, so that the plane of the nibless loop is inclined (e.g. offset) at an angle to the longitudinal axis of the flexible actuator shaft. This configuration may assist in locating the loop of wire over a sessile polyp on the wall of the colon.

The length of wire may be roughened or sharpened over its surface (or on the surface which forms the inner surface of the fixed circumference loop) to facilitate cutting. The length of wire may have a cable-like structure formed from a plurality of strands that are woven, twisted, braided or otherwise joined together. The plurality of strands may be made from nitinol. The plurality of strands may include one of more strands made from a barbed wire. This structure may assist the wire in gripping small sessile polyps.

The end cap and nibless loop of wire may be detachably mounted on the flexible actuator shaft, e.g. using a suitable bayonet connection or the like. This may allow loops of differing diameters to be easily interchangeable.

In another embodiment, the nibless loop of wire may have a first end attached to an inner surface of the catheter and a second end connected to the inner push rod. In this arrangement, the loop of wire acts against the reaction surface in a similar manner to a cheese wire. To enable full retraction of the loop of wire against the reaction surface, the first end may be attached at a point on the inner surface of the catheter that is displaced proximally from the distal end of the catheter. It may be desirable for the end cap to have an outlet for the nibless loop of wire that is in close proximity to the attachment point of the inner surface of the catheter, so that the diameter of the loop is very small (preferably zero) when the wire is fully retracted.

To provide a precise cut, the reaction surface may have a blade mounted thereon. For safety, a distal edge of the blade is preferably located proximally to a distal end of the catheter, i.e. within the catheter. In other words, the blade may be mounted in a recess formed in the reaction surface.

The surgical snare of the invention may be used with a conventional scoping apparatus (e.g. endoscope or colonoscope). A proximal end of the flexible actuator shaft may extend out of the scoping apparatus where it is received in an actuator tool. The actuator tool may comprise a handle for applying rotation to the flexible actuator shaft, which rotation may be transferred to the distal end of the snare to turn the loop of wire. In embodiments without a separate catheter, rotation may be applied to the inner push rod, and the end cap may include a rotation joint to permit rotation of the nibless loop of wire. The actuator tool may further comprises a slider mechanism attached to the inner push rod, which enables the inner push rod to slide axially relative to the outer sleeve to deploy the loop of wire. The slider mechanism may include a gearing system, e.g. having a ratio of 2:1 or 3:1 to give the operator fine control over the opening and closing of the loop of wire. A rack and pinion type arrangement may be suitable for the gearing mechanism.

In one example, the slider mechanism may include a force limiter to limit the force that can be applied when closing the nibless loop of wire. This may prevent accidental cutting of muscle tissue which could be captured within the tissue gathered by the snare. The force limiter may be adjustable, or may only become effective when the diameter of the nibless loop of wire is small enough for cutting to begin. In one example, the inner pull wire may include a portion that exhibit elasticity in the longitudinal direction, whereby if a force on the inner pull wire exceeds a threshold, the pull wire will extend elastically rather than act to move the nibless loop of wire through the end cap.

The use of a nibless loop of nitinol wire in a surgical snare that does not require a reaction surface may be another aspect of the invention.

BRIEF DESCRIPTION OF THE DRAWINGS

Examples of the present invention are discussed in detail below with reference to the accompanying drawings, in which:

FIG. 1 is a schematic view of a colonoscope having an surgical snare that is an embodiment of the invention in the instrument channel thereof;

FIG. 2 is a schematic partial cross-sectional view of a surgical snare that is an embodiment of the invention;

FIG. 3 is a close up view of an end cap structure suitable for use with a surgical snare according to the invention;

DETAILED DESCRIPTION; FURTHER OPTIONS AND PREFERENCES

Figure 4:
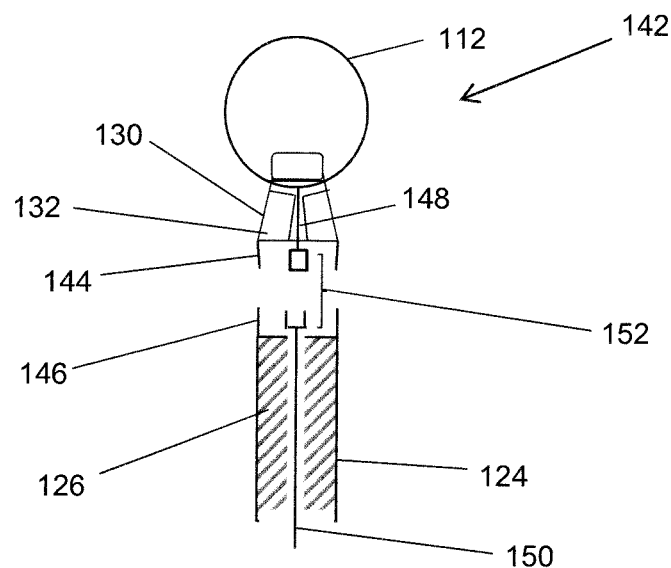
FIG. 4 is a schematic exploded partial cross-sectional view of a surgical snare that is another embodiment of the invention.

FIG. 1 is a schematic view of a colonoscope system 100 in which the surgical snare of the invention may be used. The system 100 comprises a colonoscope that has a main body 102 and a flexible shaft 104 extending from the main body, which is suitable for insertion into the body to access the treatment site. The shaft 104 houses various channels, e.g. an instrument channel and an observation channel (not shown) as is conventional. The observation channel may carry optical equipment suitable for delivering an image of the treatment site to an observation port 106.

The main body 102 includes an instrument port 108 for receiving a surgical instrument (in this case a surgical snare) into the instrument channel. As explained in more detail below, the surgical snare comprises an flexible catheter 110 which has at its distal end a loop of wire 112 forming the operative part of the snare. The loop of wire 112 is connected to a flexible actuator shaft (not shown in FIG. 1) which is conveyed by the catheter 110.

The catheter 110 is connected at its distal end to a rotator 114, which acts to rotate the catheter (and therefore the loop of wire 112) relative to the instrument channel. The flexible actuator shaft is connected at the distal end of the catheter to a slider 116, which operates to extend and retract the loop of wire 112 as discussed in more detail below.

FIG. 2 is a partial cross-sectional view of the distal end of a surgical snare that is an embodiment of the invention. In this example, the snare comprises a catheter 110 which is sized to pass through the instrument channel 118 of a scoping device (e.g. colonoscope or endoscope). As shown in FIG. 2, it is preferably for there to be an air gap 120 (the magnitude of which is exaggerated in the drawing) between the inner wall of the instrument channel 118 and the outer wall of the catheter 110. This air gap may enable suction to be applied through the instrument channel during treatment.

The catheter 110 has a tip section 122 which narrows in diameter towards the distal end. The tip section 122 may thus resemble a cone. This arrangement provides a narrow aperture for introducing the snare, which facilitates control by the surgeon.

In this example, the catheter 110 is shown as a separate entity to an outer sleeve 126 of the flexible actuator shaft 124, whereby the flexible actuator shaft 124 is slidable relative to the catheter 110. However, in an alternative example, a separate catheter 110 is not provided, and the outer sleeve 126 itself forms the catheter. Thus references herein to the catheter 110, and any features of the catheter 110, may be understood to apply equally to the outer sleeve 126 where a separate catheter 110 is not present.

The catheter 110 (and/or outer sleeve 126) is a flexible hollow tube that carries the flexible actuator shaft 124. The material for the catheter is chosen to exhibit sufficient stiffness to facilitate pushing through the colonoscope. The catheter may be made from nylon, PTFE, FEP, braided FEP, PFA, ETFE, PEEK or the like.

The flexible actuator shaft 124 comprises an outer sleeve 126 which is slidably received in the catheter 110 and an inner push rod 128, e.g. a wire of stainless steel or the like, which is slidably received in the outer sleeve 126.

The flexible actuator shaft 124 terminates at its distal end with an end cap 130, which is a rigid unit, e.g. made from stainless steel. In this embodiment, the end cap 130 is shaped to fit against the tip section 122 of the catheter 110 in manner that enables the loop of wire 112 to extend out of the catheter 110. For example, the end cap may comprises side surfaces which cooperate with the inside surface of the tip section 122.

FIG. 2 shows the end cap in cross-section, with a T-shaped internal passageway for receiving the loop of wire 112 and internal push rod 128.

FIG. 3 shows a side view of the end cap 130 when rotated 90° around a vertical axis from the position shown in FIG. 2. Here it can be appreciated that the end cap 130 is formed in two pieces, which are secured together, e.g. by welding or the like, after the loop of wire 112 and inner push rod 128 are mounted therein. The end cap 130 thus comprises a base 132 that is attached to the outer sleeve 126. In this embodiment, the base 132 has a tapered shape, but any shape suitable for sliding within the catheter 110 may be used. The base 132 has a T-shaped channel 134 formed therein. The top (crossbar) of the T-shaped channel 134 is open at the top surface and side surfaces of the base 132, e.g. to form a channel. The bottom of the T-shaped channel 134 is open to provide an outlet for the inner push rod 128. To secure the loop in the T-shaped channel 134, the end cap 130 includes a top piece 136 which is secured (e.g. welded) to the top surface of the base 132 to close the channel. The top piece 136 may include a ridge 138 the fits into the channel in the top surface of the base 132, e.g. to improve the structural integrity of the component. The top surface of the top piece 136 may have a groove 140 formed therein for receiving the loop of wire 112 when the snare is fully retracted.

The loop of wire 112 is preferably made from a material that has sufficient rigidity and resilience to adopt a round shape when extended from the end cap. The inventors have found that alloys which exhibit shape memory properties, e.g. nickel titanium (nitinol) are particularly well suited.

Furthermore, in the invention, the loop of wire 112 has a fixed circumferential length, i.e. two ends of a single length of wire (e.g. nitinol) are attached together (e.g. by welding) to form a loop. The diameter of the loop may be any suitable size, e.g. up to 20 mm, but preferably 10 mm or less, more preferably less than 8 mm. If the material has shape memory properties, the loop may be trained to occupy a predetermined shape at rest. An advantage of using this loop configuration is that the shape may be uniformly round, i.e. without discontinuities such as kinks or nibs. This enables the loop to be fully closed against the end cap 130, which reduces or eliminates the risk of an incomplete cut.

Once formed in this manner, the loop of wire 112 may be attached, e.g. welded or otherwise secured, to the inner push rod 128, which may be of stainless steel or other material that exhibits sufficient rigidity. The inner push rod 128 may meet the loop of wire 112 at a T-junction, which may fit in the T-shaped channel when the snare is fully deployed (extended). Sliding the inner push rod 128 relative to the outer sleeve 126 causes the loop of wire to be drawn into or out of the end cap 130. The outer sleeve 126 and inner push rod 128 may thus act as a dual action deployment shaft, which both locates the loop of wire 112 relative to the catheter 110 and deploys (extends and retracts) the loop of wire 112.

In use, the loop of wire 112 gathers biological tissue and draws it back towards the end cap as the snare is retracted. The top surface of the top piece 136 (with or without the groove 140) may thus act as a reaction surface against which the loop of wire may press the tissue to perform mechanical (pressure) cutting/resection. Although the top surface is shown to be flat in FIG. 2, in practice it may be also be convex, e.g. to match the shape of the loop as it is closed.

To assist the cutting function, the loop of wire 112 may be provided with a roughened surface, e.g. on the inwardly facing part thereof.

The inner push rod 128 may be operable by a conventional slider located at the proximal end of the catheter. The slider may include a gearing mechanism, e.g. having a 3:1 gearing ratio to assist in the fine movements that may be required at the distal end.

FIG. 4 shows another embodiment of a surgical snare. Features in common with the snare shown in FIG. 2 are given the same reference numbers and are not described again. In this embodiment, the surgical snare comprises a detachable snare head 142 that can be coupled to the flexible actuator shaft 124. The detachable snare head 142 includes the loop of wire 112 and end cap 130 discussed above. However, the base 132 of the end cap 130 and the distal end of the flexible actuator shaft 124 have cooperating attachment elements 144, 146 which are engageable to secure the end cap 130 to the flexible actuator shaft 124. The cooperating attachment elements 144, 146 may comprises interlocking feature, e.g. a bayonet fitting, or may include screw threads, a spring clip, a tie-wrap fastening or other means of securing components in an axial sense.

In this embodiment, the function of the inner push rod 128 is provided by a distal coupling rod 148 and a proximal coupling rod 150. The distal coupling rod 148 is attached (e.g. welded) to the loop of wire 112, and the proximal coupling rod 150 travels through the outer sleeve 126 from the slider (not shown) at the proximal end of the catheter 110. The distal coupling rod 148 and proximal coupling rod 150 engage with each other through a coupling 152 when the end cap 130 is secured to the flexible actuator shaft 124. When engaged, the distal coupling rod 148 and the proximal coupling rod 150 act as a single rigid entity that performs the function of the inner push rod 128.

Figure 5:
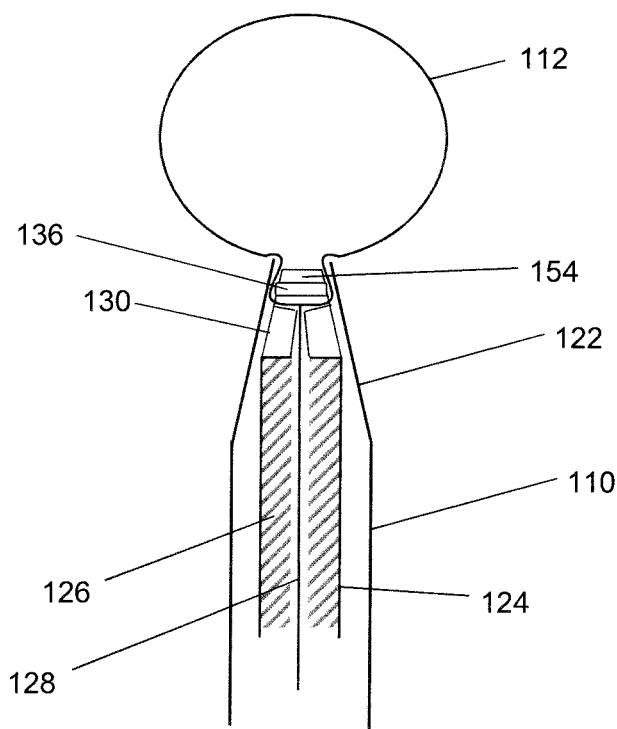
FIG. 5 is a schematic partial cross-sectional view of a surgical snare that is yet another embodiment of the invention.

FIG. 5 shows another embodiment of a surgical snare. Features in common with the snare shown in FIG. 2 are given the same reference numbers and are not described again. In this embodiment, a sharp edge or blade 154 is attached to or integrally formed with the top surface of the end cap 130 (i.e. as part of the reaction surface mentioned above). The blade 154 may further assist in obtaining a clean cut.

To prevent the blade 154 from accidentally damaging surround tissue at the treatment site (i.e. tissue not gathered within the loop of wire 112, the blade 154 and/or end cap 130 may be configured to ensure that they reside fully within the catheter 110. In other words, the distal edge of the blade 154 is located proximally to the distal end of the tip section 122 of the catheter 110. The end cap 130 may include gaps or channels in the side walls of the top piece 136 to permit the loop of wire 112 to pass out beyond the catheter 110.

Figure 6:
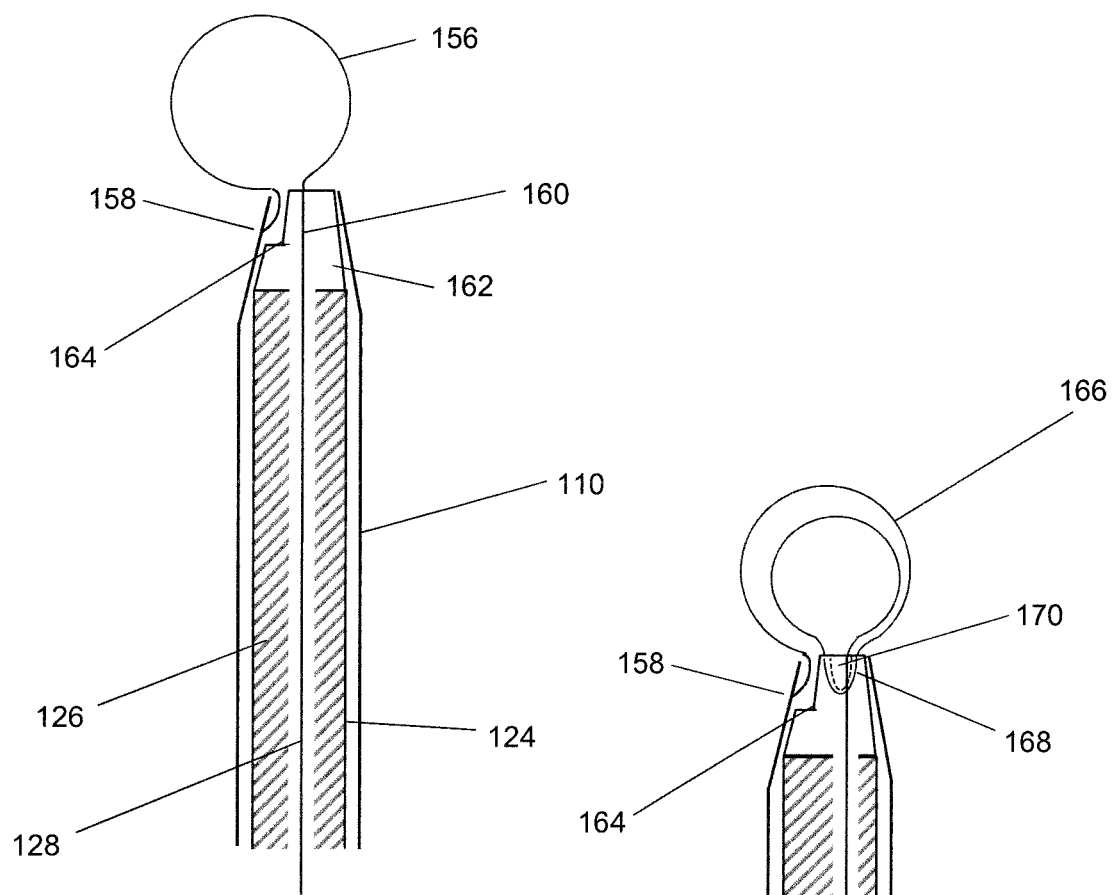
FIG. 6 is a schematic partial cross-sectional view of a surgical snare that is yet another embodiment of the invention.

FIG. 6 shows another embodiment of a surgical snare. Features in common with the snare shown in FIG. 2 are given the same reference numbers and are not described again. In this embodiment, the operative part of the snare is formed by a looped length of wire 156. Unlike the previous embodiments, the ends of the length of wire 156 forming the loop are not attached. Instead, one end 158 is attached to an inside surface of the catheter 110, e.g. in the tip section 122 thereof. The point of attachment is set back from the distal end of the tip section to allow the loop to be full retracted.

The other end 160 of the length of wire 156 is attached, e.g. welded, to the distal end of the inner push rod 128. As described above, the length of wire 156 may be formed from an alloy that exhibits shape memory properties (e.g. nitinol) so that it tends to adopt a looped configuration when extended out of the catheter 110.

As in the embodiments described above, an end cap 162 terminates the distal end of the flexible actuator shaft 124. In this embodiment, the end cap 162 may comprise an axial passageway through which the length of wire 156 (and inner push rod 128) travel during deployment of the snare. The end cap 162 may thus be formed as a single piece (e.g. of stainless steel).

The end cap 162 may have a channel 164 or gap formed in its outer surface to permit the length of wire to travel past it from the attachment point inside the catheter 110.

In use, the length of wire may act like a cheese wire to pull biological tissue encircled by the loop against the top surface of the end cap 162.

Figure 7:
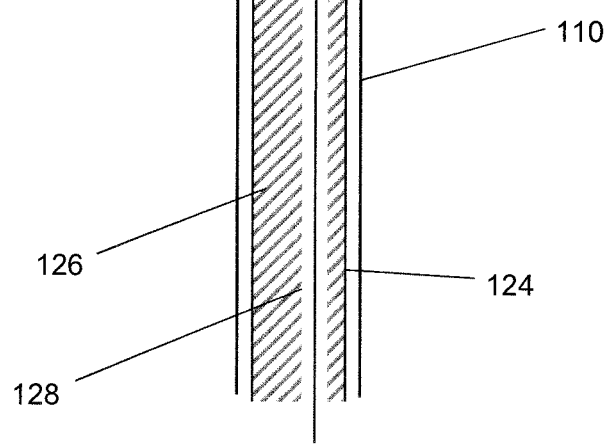
FIG. 7 is a schematic partial cross-sectional view of a surgical snare that is yet another embodiment of the invention.

FIG. 7 shows another embodiment of a surgical snare. Features in common with the snare shown in FIG. 6 are given the same reference numbers and are not described again. In this embodiment, the operative part of the snare is formed by a double looped length of wire 166. In this embodiment, the end cap includes a U-shaped passage 168 for receiving a portion of the double looped length of wire 166. This has the effect of utilising the force used to close the loop as means for supporting the reaction surface, which may give greater control over the cutting process. Moreover, in one example, the end cap may include a movable tip portion 170 (which may be biased back into the end cap by a spring or the like) which can be brought out of the end cap into contact with tissue gather in the loop during closure of the loop. The movable tip portion 170 may have a sharpened distal edge or a blade mounted thereon.

Figure 8A:
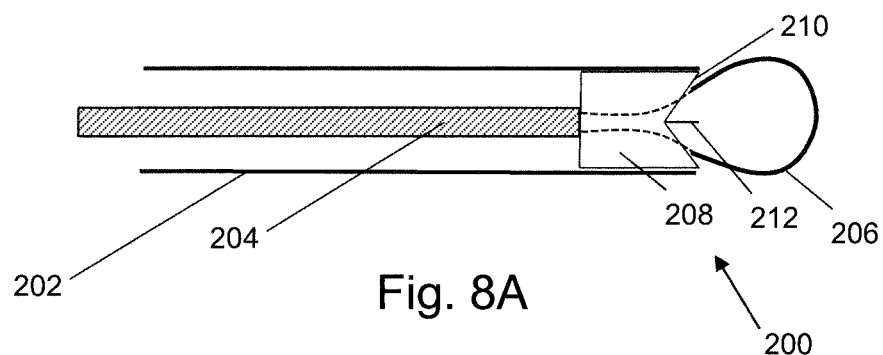
FIGS. 8A, 8B, 8C are schematic cross-sectional views through three alternative end cap configurations.

FIG. 8A shows a schematic cross-sectional view through a distal end of a snare device 200 according to another embodiment. The snare device 200 comprises a flexible actuator shaft comprising an outer sleeve 202 (e.g. made form nylon) and an inner push rod 204 (e.g. made from stainless steel) that is mounted within and slidable relative to the outer sleeve 202. A nibless loop of wire 206 is connected to a distal end of the inner push rod. The loop of wire may be made of a plurality of braided nitinol strands or a single nitinol strand. In this example, both ends of the loop are connected to the push rod 204. However, it is also possible that one end is fixed to the end cap 208 (e.g. in the internal passageway) and the other end connected to the push rod 204. The loop of wire 206 in slidable by the action of the push rod 204 through an end cap 208 that is mounted at a distal end of the outer sleeve 202. The end cap may be made from stainless steel. The end cap 208 has an internal passageway (not shown) for receiving the nibless loop of wire. In this embodiment, the end cap 208 has an indented distal surface 210 from which projects a thin blade 212. The blade 212 spans across the entrance to the internal passageway to provide a reaction surface against which the nibless loop of wire 206 bears when fully retracted into the end cap 208. The blade assists cutting of tissue captured in the loop. The indented distal surface ensures that the tip of the blade does not project substantially beyond the end of the outer sleeve 202.

Figure 8B:
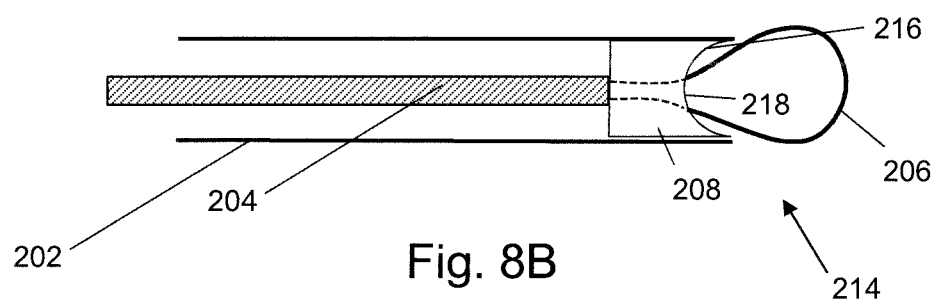

FIG. 8B shows a schematic cross-sectional view through a distal end of a snare device 214 according to another embodiment. Features in common with FIG. 8A are given the same reference number and are not described again. In this embodiment the end cap 208 comprises a pair of internal passageways, one for each end of the loop 206. The end cap 208 has a concave distal face 216 that is sharpened in a cutting region 218 between the entrances to the internal passageways. The cutting region 218 forms a reaction surface against which the nibless loop of wire 206 bears when fully retracted into the end cap 208. The concave distal face 216 ensures that the cutting region does not project beyond the end of the outer sleeve 202.

Figure 8C:
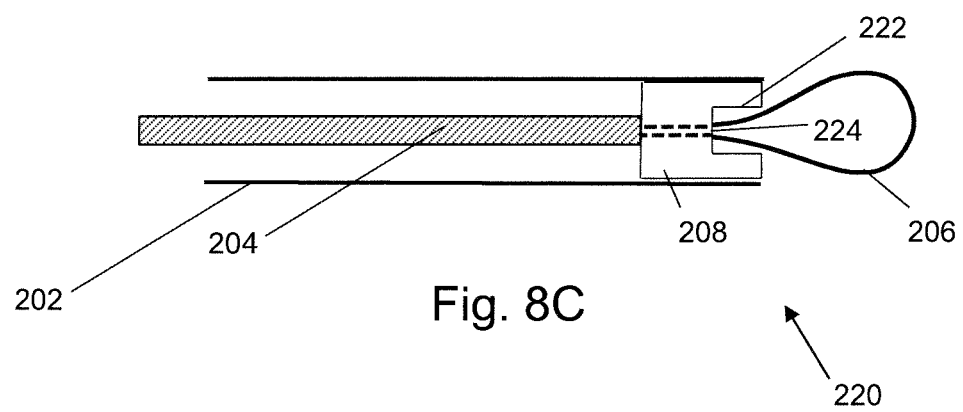

FIG. 8C shows a schematic cross-sectional view through a distal end of a snare device 220 according to another embodiment. Features in common with FIG. 8A are given the same reference number and are not described again. In this embodiment the end cap 208 also comprises a pair of internal passageways (not shown), one for each end of the loop 206. The end cap 208 has a recessed mouth 222, and the distal end of the pair of passageway open into the base of the recessed mouth. The base of the recessed mouth 222 is sharpened in a cutting region 224 between the entrances to the internal passageways. The cutting region 224 forms a reaction surface against which the nibless loop of wire 206 bears when fully retracted into the end cap 208. The recessed mouth 222 ensures that the cutting region does not project beyond the end of the outer sleeve 202.

In all of the embodiments discussed above, the loop of wire extends distally from the tip section of the catheter. In other embodiments, the passageway in the snare cap may open through a side surface of the tip section, so that the loop of wire is directed to one side of the device.

The invention claimed is:

1. A surgical snare comprising: a flexible actuator shaft comprising an outer sleeve and an inner push rod mounted within and slidable relative to the outer sleeve; an end cap mounted at a distal end of the outer sleeve; a nibless loop of wire connected to a distal end of the inner push rod, and configured to capture biological tissue, wherein the end cap includes a passageway for receiving the nibless loop of wire, whereby the inner push rod is operable to retract the nibless loop of wire into the end cap, and wherein the end cap includes a reaction surface at its distal end against which the nibless loop of wire is configured to cut biological tissue captured within the nibless bop of wire when fully retracted into the end cap such that the nibless loop of wire bears against the reaction surface resulting in the nibless loop of wire and the reaction surface cutting the biological tissue.

2. A surgical snare according to claim 1, wherein the reaction surface is a flat or concave distal face of the end cap.

3. A surgical snare according to claim 1, wherein the reaction surface includes a groove for receiving the nibless loop of wire when fully retracted into the end cap.

4. A surgical snare according to claim 1, comprising a catheter, wherein the flexible actuator shaft is slidably mounted in the catheter to deploy the end cap at a distal end thereof.

5. A surgical snare according to claim 4, wherein the catheter has a tip section that narrows towards a distal end of the catheter.

6. A surgical snare according to claim 4, wherein there is a fluid flow path around the catheter to permit a suction force to be applied beyond the distal end of the catheter.

7. A surgical snare according to claim 1, wherein the outer sleeve forms a catheter that is slidably receivable in an instrument channel of a surgical scoping device.

8. A surgical snare according to claim 1, wherein the nibless loop of wire comprises a fixed circumference loop formed from a length of wire whose two ends are attached together.

9. A surgical snare according to claim 8, wherein the nibless loop of wire is connected to the inner push rod at a junction between the two ends of the length of wire.

10. A surgical snare according to claim 8, wherein the length of wire is a shape memory alloy trained to preferentially adopt a round shape.

11. A surgical snare according to claim 10, wherein the round shape is a circle having a diameter of 10 mm or less.

12. A surgical snare according to claim 8, wherein the length of wire is made from nitinol.

13. A surgical snare according to claim 8, wherein the inner surface of the fixed circumference loop is roughened to facilitate cutting.

14. A surgical snare according to claim 1, wherein the end cap and nibless loop of wire are detachably mounted on the flexible actuator shaft.

* * * * *